United States Patent
Hirschel et al.

(10) Patent No.: US 11,224,697 B2
(45) Date of Patent: Jan. 18, 2022

(54) INJECTION UNIT FOR ADMINISTERING OR DELIVERING A FLUID PRODUCT

(71) Applicant: Ypsomed AG, Burgdorf (CH)

(72) Inventors: Juerg Hirschel, Bern (CH); Ulrich Moser, Heimiswil (CH); Stefan Burren, Schwarzenburg (CH)

(73) Assignee: Ypsomed AG, Burgdorf (CH)

( * ) Notice: Subject to any disclaimer, the term of this patent is extended or adjusted under 35 U.S.C. 154(b) by 323 days.

(21) Appl. No.: 16/378,885

(22) Filed: Apr. 9, 2019

(65) Prior Publication Data

US 2019/0231987 A1 Aug. 1, 2019

Related U.S. Application Data

(63) Continuation of application No. 15/809,633, filed on Nov. 10, 2017, now Pat. No. 10,471,215, which is a (Continued)

(30) Foreign Application Priority Data

Feb. 9, 2012 (CH) .......................................... 177/12

(51) Int. Cl.
*A61M 5/00* (2006.01)
*A61M 5/315* (2006.01)

(52) U.S. Cl.
CPC ...... *A61M 5/3156* (2013.01); *A61M 5/31551* (2013.01); *A61M 5/31585* (2013.01); (Continued)

(58) Field of Classification Search
CPC ...... A61M 5/31551; A61M 2005/3154; A61M 2205/581; A61M 2205/582;
(Continued)

(56) References Cited

U.S. PATENT DOCUMENTS

| 5,626,566 A | 5/1997 | Petersen et al. |
| 5,674,204 A | 10/1997 | Chanoch |

(Continued)

FOREIGN PATENT DOCUMENTS

| DE | 102007026083 A1 | 11/2008 |
| EP | 1003581 A1 | 5/2000 |

(Continued)

OTHER PUBLICATIONS

"International Report on Patentability", regarding PCT/CH2013/000021, 12 pages, dated Aug. 12, 2014.

(Continued)

*Primary Examiner* — Rebecca E Eisenberg
(74) *Attorney, Agent, or Firm* — Dorsey & Whitney LLP (57) ABSTRACT

The invention relates to an injection unit, preferably a pen-shaped injection unit, for administering or delivering a fluid product. The injection unit comprises a housing, an axially movable piston rod mounted in the housing in a non-rotatable manner, a delivery apparatus having a threaded nut that is able to move the piston rod in order to deliver product, a dosing device having a dosing sleeve, a rotary knob, a discharge button arranged coaxially on the dosing sleeve, and a receptacle for the product. The dosing device is connected to the delivery apparatus via a coupling mechanism, wherein the coupling mechanism includes of at least two coupling surfaces that each carry a toothing comprising teeth, wherein the coupling surfaces are used to generate an acoustic and/or tactile signal corresponding to the set or corrected dose of the product to be administered during the dosing operation or during correction of the dose.

10 Claims, 8 Drawing Sheets

Related U.S. Application Data continuation of application No. 14/454,572, filed on Aug. 7, 2014, now Pat. No. 9,821,121, which is a continuation of application No. PCT/CH2013/000021, filed on Feb. 5, 2013.

(52) U.S. Cl.
CPC . *A61M 5/31535* (2013.01); *A61M 2005/3154* (2013.01); *A61M 2205/581* (2013.01); *A61M 2205/582* (2013.01)

(58) Field of Classification Search
CPC ............ A61M 5/31535; A61M 5/3156; A61M 5/31585; A61M 5/31583; A61M 5/31568; A61M 5/20; A61M 5/31553
See application file for complete search history.

(56) References Cited

U.S. PATENT DOCUMENTS

| | | |
|---|---|---|
| 5,827,232 A | 10/1998 | Chanoch et al. |
| 6,248,095 B1 | 6/2001 | Giambattista |
| 6,936,032 B1 | 8/2005 | Bush, Jr. et al. |
| 2004/0127858 A1 | 7/2004 | Bendek et al. |
| 2007/0016142 A1 | 1/2007 | Burren et al. |
| 2008/0183138 A1 | 7/2008 | Moser et al. |
| 2009/0275916 A1 | 11/2009 | Harms et al. |
| 2011/0257604 A1* | 10/2011 | Banik ............... A61M 5/484 604/209 |
| 2014/0046268 A1 | 2/2014 | Quinn et al. |
| 2014/0094765 A1 | 4/2014 | Pala |
| 2018/0078706 A1 | 3/2018 | Hirschel et al. |

FOREIGN PATENT DOCUMENTS

| | | |
|---|---|---|
| EP | 1294418 B1 | 9/2005 |
| WO | 9307922 A1 | 4/1993 |
| WO | 0195959 A1 | 12/2001 |
| WO | 2004078242 A2 | 9/2004 |
| WO | 2004093940 A2 | 11/2004 |
| WO | 2010072229 A1 | 7/2010 |
| WO | 2011068531 A1 | 6/2011 |

OTHER PUBLICATIONS

"International Search Report", PCT Application No. PCT/CH2013/00021 Filed Feb. 5, 2013, dated May 23, 2013, 5 pages.

* cited by examiner

INJECTION UNIT FOR ADMINISTERING OR DELIVERING A FLUID PRODUCT

CROSS-REFERENCE TO RELATED APPLICATIONS

This application is a continuation of U.S. patent application Ser. No. 15/809,633 filed Nov. 10, 2017, issued as U.S. Pat. No. 10,471,215 on Nov. 12, 2019, which is a continuation of U.S. patent application Ser. No. 14/454,572, filed Aug. 7, 2014, issued as U.S. Pat. No. 9,821,121 on Nov. 21, 2017, which is a continuation of International Application No. PCT/CH2013/000021 filed Feb. 5, 2013, which claims priority to Swiss Application No. 177/12 filed Feb. 9, 2012, the contents of all of which are herein incorporated by reference.

BACKGROUND

The present invention pertains to an injection unit, particularly to an injection unit with a dosing device, by means of which a dose or quantity of a substance to be discharged from or with the aid of the injection unit can be adjusted.

Various injection units, particularly also pin-shaped or pen-shaped injection units, are known from the prior art. For example, WO 93/07922 A1 discloses such a pin-shaped or pen-shaped injection unit. The pen comprises a dosing device and a delivery apparatus that are coupled to one another by means of a two-part unidirectional coupling 20/21, wherein the coupling is realized by means of asymmetric toothings that engage into one another and the engagement is promoted by means of a spring. In this case, a coupling input element 20 features a toothing that is axially directed in the distal direction. A coupling output element 21 features a complementary toothing. The two coupling elements are arranged coaxial to the longitudinal axis of the pen and realized such that they are rotatable relative to the housing of the pen. The individual teeth of the toothings have two flanks, wherein the two flanks have different inclines. One flank points in the axial direction and the second flank has an incline relative to the longitudinal axis. When the coupling is engaged, the axially aligned flanks prevent a relative rotation between the coupling input element 20 and the coupling output element 21 in one direction, whereas the second, inclined flanks allow a relative rotation in the opposite direction.

In order to adjust a dose to be administered, the dosing knob 14 of the dosing device is screwed out of the housing of the unit together with the dosing sleeve 15. In this case, the coupling input element 20 is arranged non-rotatably relative to the dosing knob 14, and the coupling output element 21 is arranged non-rotatably relative to the delivery apparatus. When the dose is increased, the pen is designed in such a way that a relative rotation can take place between the coupling input element 20 and the coupling output element 21. The inclined flanks of the coupling toothings slide over one another in this case, wherein the coupling input element 20 is axially moved against the spring force. When the tips of the teeth slide over one another, the coupling input element 20 springs back into its axial starting position along the axially aligned flanks and generates an audible click. When the dosing knob 14 is screwed back into the housing, the unidirectional coupling prevents a relative rotation between the dosing device and the delivery apparatus due to the axially aligned tooth flanks on the coupling elements 20, 21, wherein the rotation of the dosing knob is therefore transmitted to the delivery apparatus and the discharge of product from the pen can take place. In order to correct the dose, the engagement between the coupling elements 20, 21 has to be manually separated against the spring force. Once the engagement is separated, the dosing device can be moved back into its starting position independently of the delivery apparatus. In order to carry out this type of dose correction, the person using the injection unit must be skilled and powerful because both hands are required for separating and maintaining the engagement in the separated position, i.e. against the spring force. In the released state, the dosing sleeve also has to be screwed back. When the dosing sleeve is screwed back and the engagement is separated, no feedback for the user in the form of a clicking sound is therefore generated.

FIGS. 15-17 of EP 1003581 B1 also show a pen-shaped injection unit. This injection unit features a bidirectional coupling between the dosing device and the delivery apparatus. The dosing device comprises a dosing sleeve 80 with a dosing knob 81 arranged on the sleeve. The dosing sleeve 80 can be coupled to the driver tube 85 of the delivery apparatus by means of a bushing 82. The coupling consists of a coupling input element (not shown) that is rigidly arranged on the dosing sleeve 80 and a coupling output element 93 that is also referred to as rosette and is rigidly arranged on the bushing 82. The coupling is engaged by pushing the discharge button 88 in the distal direction, and it remains non-positively engaged as long as the discharge button is not actuated. The coupling input element and the coupling output element feature a toothing that, in principle, allows a relative rotation, namely even if the coupling elements contact one another due to the weights. As long as the coupling is not engaged due to an actuation of the discharge button, this allows a dosing motion in order to increase the dose, as well as to correct the dose. In the embodiment known from the prior art, no clicking sound is generated in the bidirectional coupling, so that a clicking function has to be realized separately at a different location in the unit.

It is the objective of the present invention to make available an injection unit of the above-described type, i.e. an administration unit with a dosing device and a delivery apparatus that can be separably coupled to one another by means of a coupling mechanism, which has a simple design and provides the user with feedback that can be perceived in an improved fashion during the dose adjustment and/or the correction of excessively adjusted doses.

This objective is attained by means of the object with the characteristics as claimed at least by the independent claims. Other advantageous embodiments are disclosed in the dependent claims.

SUMMARY

The present description of a generally pen-shaped injection unit contains different references to directions and positions that are briefly explained at this point. The axial orientation refers to the orientation along the longitudinal axis of the injection unit. The distal end refers to the end of the injection unit on which the injection needle is arranged. Accordingly, the proximal end is therefore the opposite end of the injection unit. In the distal direction means looking in the direction of the distal end and in the proximal direction analogously means looking in the direction of the proximal end.

The invention pertains to an improved injection unit for administering a fluid product. The injection unit comprises a housing with a receptacle for the product, a delivery apparatus for delivering the product, as well as a dosing device for adjusting a product dose to be administered and for displaying the adjusted product dose. The housing forms a receptacle for the product, preferably a receptacle for a container filled with the product. This container is preferably a carpule. The delivery apparatus comprises a piston rod that can be moved relative to the housing in a delivery direction in order to discharge an adjusted product dose in a delivery stroke that corresponds to the adjusted product dose. The delivery stroke involves of a translatory motion of the piston rod, preferably a linear sliding motion. In a preferred embodiment, a movable piston of the container realized in the form of a carpule is displaced during the delivery stroke. The delivery apparatus furthermore comprises a guide element that guides the translatory motion of the piston rod. In a preferred embodiment, the guide element is realized in the form of a longitudinal guide for the piston rod that is fixed on the housing such that the piston rod can be axially displaced relative to the guide element, but not turned. The delivery apparatus furthermore comprises a drive element that is engaged with the piston rod. In a preferred embodiment, the drive element is realized in the form of a threaded nut, the internal thread of which is engaged with a corresponding external thread arranged on the outer surface of the piston rod. The threaded nut is preferably arranged in the housing rotatably, but in an axially fixed fashion. In one potential preferred embodiment, the following kinematic arrangement is realized for the delivery mechanism of the delivery apparatus: a rotation of the axially fixed threaded nut relative to the piston rod results in an axial motion of the piston rod because it cannot turn relative to the housing due to the longitudinal guide. In other preferred embodiments, the kinematic arrangement may also be inverted. This is realized with a so-called kinematic reversal, in which the threaded nut is rotatively fixed relative to the housing and the longitudinal guide is rotatable and, if so required, displaceable relative to the housing. When the longitudinal guide is turned in this kinematic reversal, the piston rod is screwed through the thread of the threaded nut that is fixed relative to the housing in this case.

The dosing device of the injection unit comprises a dose adjusting element, preferably a rotatable dosing sleeve, which is in threaded engagement with the inner side of the housing. An element that can be grasped is arranged on the proximal end of the dose adjusting element and enables the user to adjust a desired dose. The dose adjusting element preferably carries out a rotational and translational screw-type motion out of the injection unit when a dose to be administered is increased. The dose adjusting element can then be screwed back into the injection unit in order to respectively administer the adjusted dose or reduce an excessively adjusted dose. In another preferred embodiment, a non-self-locking threaded connection is produced between the housing and the dose adjusting element realized in the form of a dosing sleeve such that the dosing sleeve can be screwed back into the injection unit by applying axial forces.

The dosing device furthermore comprises a coupling mechanism that can operatively connect and disconnect the dosing device and the delivery apparatus. In this case, the coupling mechanism is realized in such a way that the adjustment and/or correction of a dose to be administered can take place independently of the delivery apparatus (e.g., in a disconnected state), and that the dosing device selectively can be operatively coupled to the delivery apparatus when a dose is administered (e.g., in a connected state) such that a motion of the dosing device is entirely or proportionally transmitted to the delivery apparatus. For example, only the rotational component of a screw-type motion of the dosing sleeve or, alternatively, only the axial displacement may be transmitted to the delivery apparatus.

In one embodiment, the coupling mechanism of the dosing device comprises a coupling sleeve with a coupling face, wherein the coupling face features engaging elements. The dose adjusting element realized in the form of a dosing sleeve features a coupling counterface with complementary engaging elements. The coupling face and the coupling counterface can be engaged with one another by means of a coupling motion in order to inhibit a relative motion between the coupling sleeve and the dosing sleeve. In an alternative embodiment, the coupling face and the coupling counterface are always engaged with one another, wherein the coupling motion is limited to blocking a relative motion between the coupling sleeve and the dosing sleeve. In another preferred embodiment, the coupling face and the coupling counterface do not directly adjoin one another, but rather are separated by a so-called click disk. In this case, the click disk separates the relative motion of the coupling face and the coupling counterface and thus makes it possible to optimize the coupling properties. An acoustic feedback signal can be customized, in particular, with skillful profiling in the coupling faces such that it provides the user with information on the amount of the dose during the dosing operation, as well as during a dose correction or dose change.

The dosing device furthermore comprises a discharge button that is movably arranged on the proximal end of the dosing device. In a preferred embodiment of the dose adjusting element in the form of a dosing sleeve, the discharge button is arranged coaxial to the dosing sleeve on its proximal end. In this case, the discharge button is arranged, in particular, such that it is rotatable relative to the dosing sleeve and has a certain axial mobility. In a preferred embodiment, the coupling sleeve is also arranged coaxial to the dosing sleeve, wherein the coupling sleeve preferably is at least partially arranged within the dosing sleeve. In this embodiment, the coupling face of the coupling sleeve is realized in the form of an annular flange arranged on the outer surface of the coupling sleeve in the proximal region thereof. The coupling counterface of the dosing sleeve is likewise realized annularly and arranged complementary to the coupling face on the inner side of the dosing sleeve. In one potential embodiment, the engaging elements of the coupling face of the coupling sleeve and the complementary engaging elements of the coupling counterface of the dosing sleeve are oriented axially to the injection unit such that the coupling motion is an axial motion in this case. For example, the coupling can be engaged by pressing the discharge button.

The arrangement of the dosing sleeve, the coupling sleeve and the discharge button may furthermore comprise a spring that holds the coupling face of the coupling sleeve and the coupling counterface of the dosing sleeve in the engaged state. The dosing sleeve and the coupling sleeve jointly move axially during a dosing motion, wherein a rotation relative to one another is possible as long as the discharge button is not pressed and the coupling therefore is not blocked.

In a preferred embodiment, the coupling sleeve of the dosing device is secured against rotating relative to the threaded nut of the delivery apparatus, but axially movable. This allows an axial motion of the coupling sleeve relative to the threaded nut in this embodiment. If the coupling is blocked by pressing on the discharge button and the dosing sleeve is screwed into the injection unit, the coupling sleeve also participates in this motion. Due to the inability to rotate relative to the threaded nut, only the rotation is transmitted to the threaded nut and the piston rod therefore is moved axially.

In order to ensure that the drive element realized in the form of a threaded nut can only rotate in the direction which results in a motion of the piston rod in the discharging direction, i.e. in the direction that causes a discharge, a so-called reverse lock is preferably provided between the housing and the threaded nut. This reverse lock may consist of a radially directed or an axially directed reverse lock. In this case, the reverse lock is preferably realized in such a way that a rotation of the threaded nut opposite to the discharging direction is completely blocked. During a rotation in the discharging direction, the reverse lock preferably has a certain resistance or reluctance that must be overcome in order to bring about a motion of the threaded nut. This is advantageous for preventing an inadvertent discharge during the correction of an excessively adjusted dose. The rotational resistances of the reverse lock and of the coupling particularly are adapted to one another.

The axial motion of the piston rod is blocked once the maximum deliverable product quantity is reached. For this purpose, at least one stop is arranged on the proximal end of the piston rod and engages with a counterstop arranged on the drive element as soon as the maximum deliverable product quantity is discharged from the injection unit. The stop and the counterstop may act radially, i.e. perpendicular to the longitudinal axis of the injection unit, by means of threaded ends. Alternatively, the stop and the counterstop may also act axially, i.e. parallel to the longitudinal axis of the injection unit. In advantageous embodiments, axial and radial actions may also be combined with one another.

DETAILED DESCRIPTION

Figure 1:
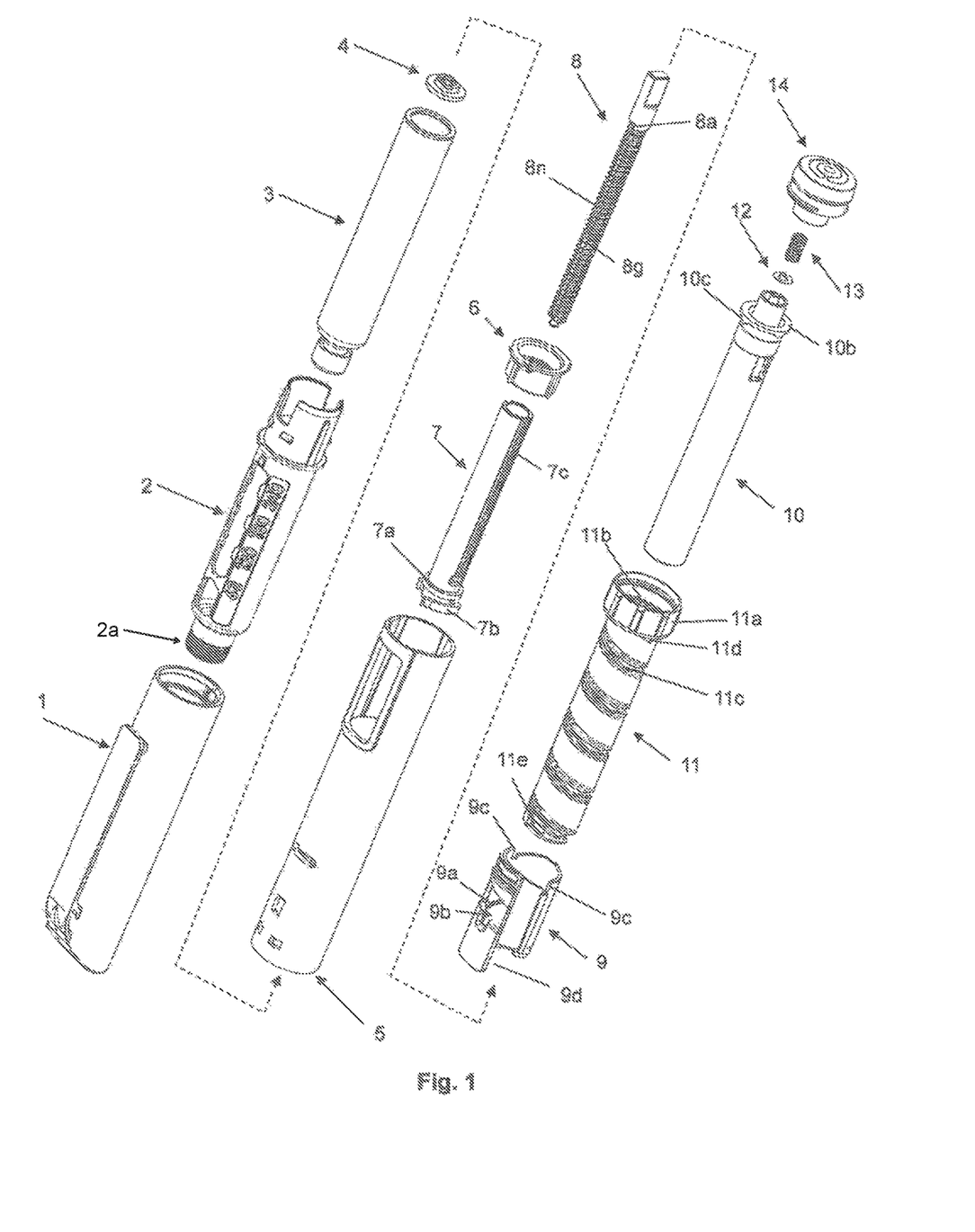
FIG. 1 shows an exploded view of the individual components of a first embodiment of an injection unit according to the invention.
Figure 2:
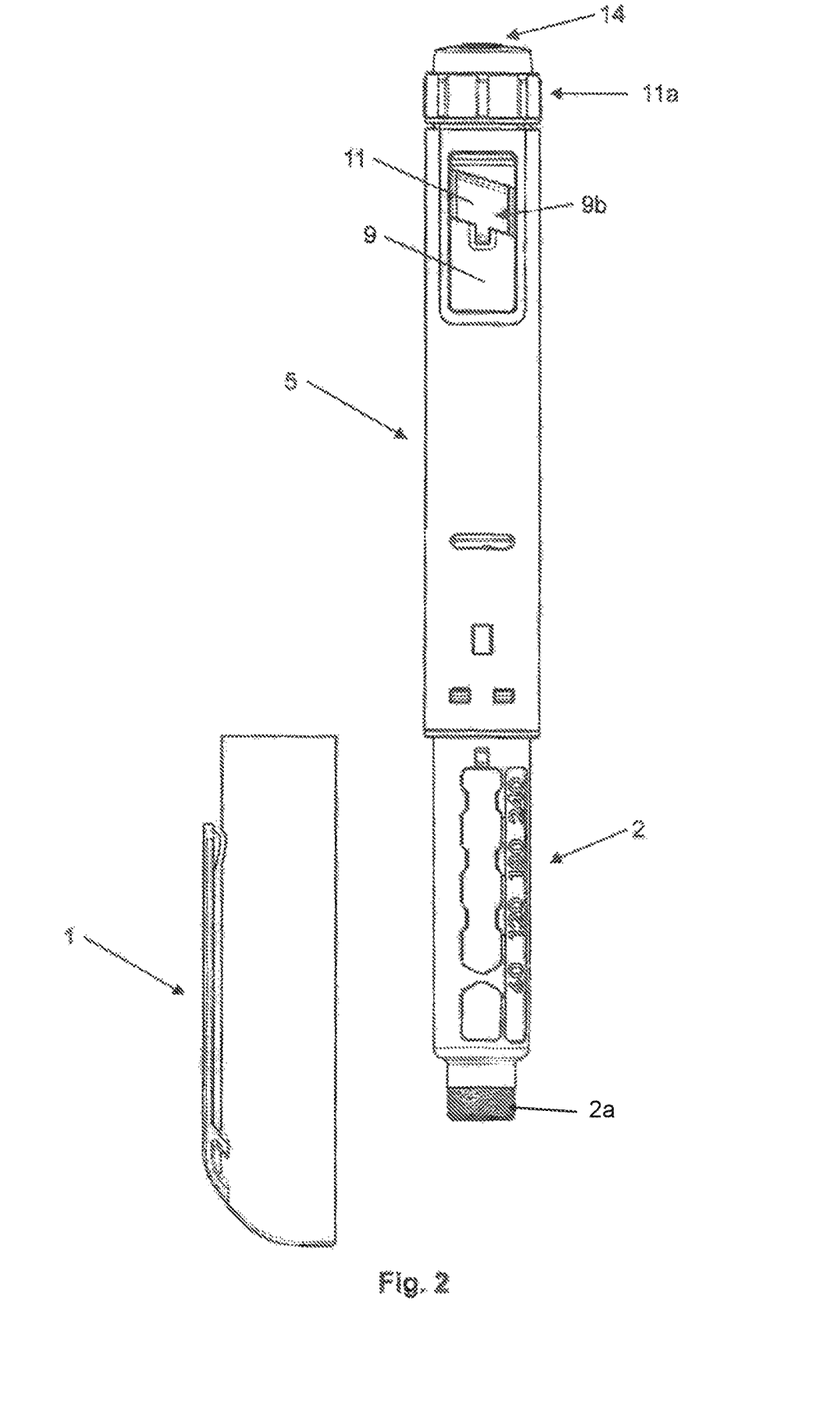
FIG. 2 shows a front view of the injection unit according to the first embodiment.
Figure 3:
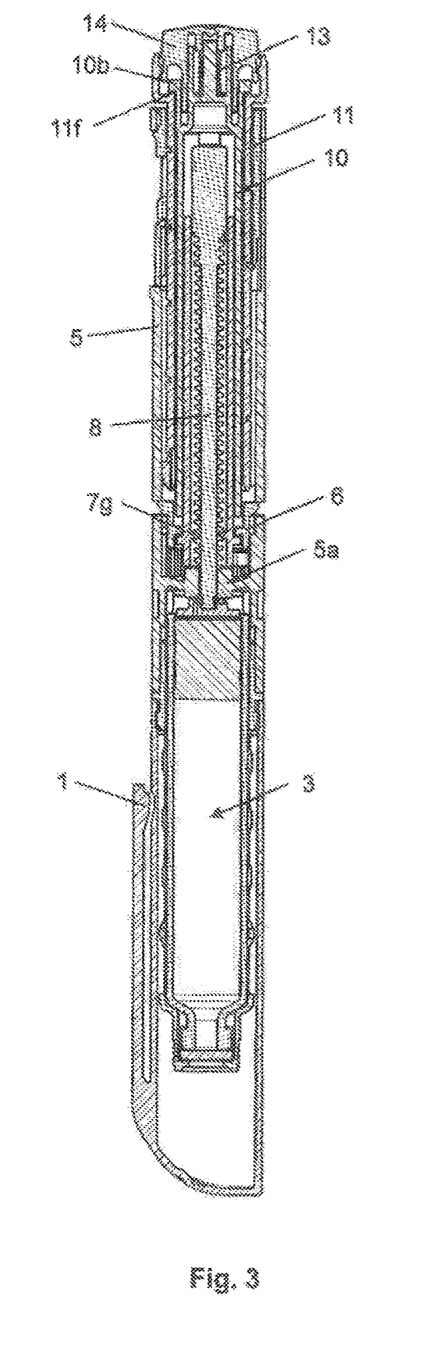
FIG. 3 shows a longitudinal section through the first embodiment in the initial state.
Figure 4:
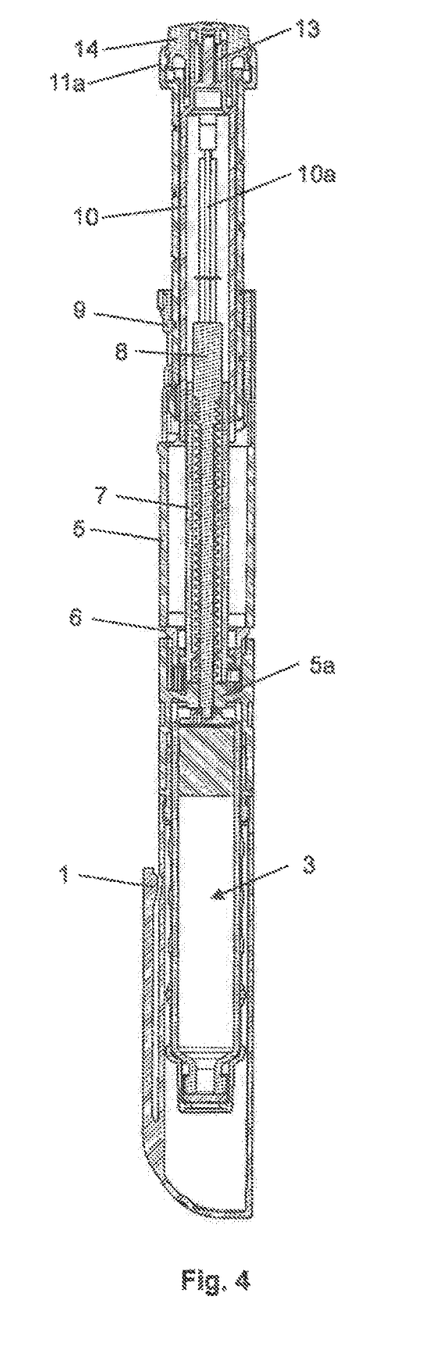
FIG. 4 shows a longitudinal section through the first embodiment once the dose has been adjusted.

FIGS. 1-4 show a first embodiment of the injection unit. FIG. 1 shows an exploded view of the individual components, FIG. 2 shows an illustration of the assembled injection unit in the delivery state, FIG. 3 shows a longitudinal section through the injection unit in the initial state before a dose is adjusted, and FIG. 4 shows the same longitudinal section, however, once the dose has been adjusted.

The housing 5 forms the base of the pen-shaped injection unit. The carpule holder 2 containing a carpule 3 is fixed on the housing 5 by means of a snap connection. The dosing device and the delivery apparatus are at least partially arranged in the housing. The threaded sleeve 9 is rigidly inserted into the housing 5. The threaded sleeve 9 has an internal thread 9a. Analogously, the threaded sleeve could also form part of the housing.

The dosing device comprises the dosing sleeve 11, the outer surface of which is at least partially provided with a thread 11c that is engaged with the internal thread 9a of the threaded sleeve 9, wherein the threaded connection between the threaded sleeve 9 and the dosing sleeve 11 is realized in a non-self-locking fashion. The rotary knob 11a for enabling the user to adjust a dose is arranged on the proximal end of the dosing sleeve 11. The dosing sleeve 11 features markings in the form of numbers on its outer surface. When the dosing sleeve 11 is screwed out of the housing 5 during the dosing operation, the adjusted dose is displayed in the window 9b of the threaded sleeve 9. FIG. 3 shows a longitudinal section through an injection unit according to the first embodiment in the initial state. The coupling 10 is arranged coaxial to the dosing sleeve 11. In its proximal region, the coupling 10 features an annular flange 10b that engages with a complementary annular counterface 11f of the dosing sleeve 11 when the coupling 10 is axially moved relative to the dosing sleeve 11 in the distal direction. The flange 10b features a toothing 10c (as illustrated in FIG. 1) that can be engaged with a corresponding (counter) toothing 11b on the counterface 11f. On the proximal end of the injection unit, a discharge button 14 is snapped on the dosing sleeve 11 in such a way that the button 14 can slightly move axially relative to the dosing sleeve 11 and is freely rotatable. In this case, the potential motion of the discharge button 14 is guided by means of corresponding guides on the proximal end of the coupling 10. A dosing click-spring 13 is arranged between the discharge button 14 and the coupling 10, optionally via washer 12. In the initial state, the spring 13 presses the discharge button in the proximal direction relative to the coupling 10. Due to the snap-on connection between the discharge button 14 and the dosing sleeve 11, the coupling 10 is consequently pressed in the distal direction relative to the discharge button 14 and the dosing sleeve 11. As a result, the flange 10b and the counterface 11f are pressed against one another by the relaxation force of the spring 13. If the dosing sleeve 11 is now turned relative to the coupling 10, the toothing of the counterface 11f slides over the toothing of the flange 10b. In this way, the coupling 10 repeatedly carries out a slight axial motion in the proximal direction and back into the starting position. If the toothing is suitably shaped, the relative rotation between the dosing sleeve 11 and the coupling 10 generates a clicking sound that can be perceived by the user acoustically, as well as in a tactile fashion. A relative rotation between the coupling 10 and the dosing sleeve 11 is inhibited when the discharge button 14 is pressed in the distal direction against the spring force such that the coupling 10 and the dosing sleeve 11 are secured against rotating relative to one another.

According to FIGS. 1 and 4, the coupling 10 is realized in the form of a sleeve. On its inner surface, it features two opposing and axially oriented guides 10a that are realized in the form of ribs. These ribs engage into corresponding guides 7c that are realized in the form of axially extending grooves in the outer surface of a threaded nut 7. Similar to the coupling 10, the threaded nut 7 is also realized in the form of a sleeve and arranged in the injection unit coaxial to the coupling 10, as well as at least partially surrounded by the coupling 10. The threaded nut 7 is rotatable in the housing 5, but arranged in an axially fixed fashion. The threaded nut 7 is held in the distal direction by a piston rod guide 5a of the housing 5, wherein the threaded nut 7 is held in the proximal direction by the housing insert 6 with the aid of the flange 7a. The housing insert 6 is rigidly snapped to the housing 5. Alternatively, it could also form part of the housing 5. On its inner side, the threaded nut 7 features a thread that is engaged with the external thread 8g of the piston rod realized in the form of a threaded rod 8. The threaded rod 8 can be axially displaced relative to the housing 5, but is secured against rotating by the piston rod guide 5a. For this purpose, the threaded rod 8 features longitudinal grooves 8n. Due to the piston rod guide 5a, a rotation of the threaded nut 7 relative to the threaded rod 8 inevitably causes an axial motion of the threaded rod 8 relative to the threaded nut 7 and the housing 5. On its distal end, the threaded nut 7 is provided with flexible arms 7b that respectively feature a tooth on their free end. The flexible arms 7b extend roughly radially outward such that the teeth arranged thereon engage with a grating (not shown) on the inner side of the housing. For this purpose, the flexible arms 7b are prestressed, in particular, in the radial direction as soon as the threaded nut 7 is inserted into the housing 5. The flexible arms 7b, the teeth and the grating are shaped in such a way that the threaded nut 7 can only rotate in one direction, wherein a certain mechanical resistance or so-called reluctance must be overcome. In the embodiment illustrated in FIG. 1, the threaded nut 7 can rotate in the direction which results in a motion of the threaded rod 8 in the distal direction. In the present embodiment, it is therefore not possible to move the threaded rod 8 in the proximal direction. A flange 4 is arranged on the distal end of the threaded rod 8 and can directly act upon the stopper of the carpule 3. When the threaded rod 8 is displaced in the distal direction, axial forces can therefore be transmitted from the threaded rod 8 to the stopper of the carpule 3 by means of the flange 4, wherein a displacement of the stopper of the carpule 3 in the distal direction results in a discharge of product when the injection needle is attached. Since the threaded nut 7 rotates relative to the housing 5 during the discharge, the flexible arms 7b also move relative to the housing 5 and their teeth move over the housing grating, wherein this generates an acoustic signal that can be perceived by the user in a tactile fashion and used as discharge feedback.

The function of the first embodiment of the injection unit is briefly explained below. The first embodiment is designed in the form of a so-called disposable pen. This means that the injection unit is completely assembled and contains the product to be administered when it is provided to the user. The user therefore only needs to evacuate the air from the injection unit prior to its use, wherein this process is also referred to as priming. The typical sequence of an injection process may take place as follows: the user removes the protective cap 1 from the injection unit and fixes an injection needle (not shown) on the needle holder 2a. The dose can now be adjusted by means of the rotary knob 11a of the dosing sleeve 11. For this purpose, the rotary knob 11a is turned such that the dosing sleeve 11 is screwed out of the injection unit. The dosing sleeve 11 is screwed out of the injection unit until the desired dose is displayed in the window 9b. If an excessive dose is inadvertently adjusted, the dose can be corrected by turning the rotary knob 11a in the opposite direction such that the dosing sleeve 11 is screwed back into the housing 5. The dosing device limits the highest adjustable dose to a predefined value. If it is attempted to screw the dosing sleeve out of the housing 5 beyond this value, the interaction between the radial stop 11e on the dosing sleeve 11 and the counterstop 9d on the threaded sleeve 9 prevent additional turning of the dosing sleeve 11.

During dosing motions and correcting motions, the dosing sleeve 11 rotates relative to the coupling 10 such that a clicking sound is generated due to the relative motion between the toothings 10c of the coupling 10 and the toothings 11b of the dosing sleeve 11. Once the desired dose is adjusted, the injection needle can be inserted into the body of the user at the intended location. The user then presses the discharge button 14 in the distal axial direction and thus blocks a relative rotation between the coupling 10 and the dosing sleeve 11. When additional pressure is applied in the distal axial direction, the dosing sleeve begins to carry out a screw-type motion back into the housing. Since the dosing sleeve 11 and the coupling 10 are secured against rotating relative to one another, the coupling 10 carries out the same motion as the dosing sleeve 11. The rotational motion of the dosing sleeve 11 is transmitted to the threaded nut 7 because the coupling 10 is permanently secured against rotating relative to the threaded nut 7. However, since the coupling 10 is arranged on the threaded nut 7 in an axially displaceable fashion, no axial forces are transmitted to the threaded nut 7. As already mentioned above, the rotating threaded nut 7 generates an axial motion of the threaded rod 8 in the distal direction. During this process, the flange 4 acts upon and likewise displaces the stopper of the carpule 3 in the distal direction in accordance with the displacement of the threaded rod 8, wherein the previously adjusted dose can now be respectively discharged or administered.

Once the dose has been administered, i.e. once the dosing sleeve has been completely screwed back into the housing 5, radial stops (11d, 9c) on the dosing sleeve 11 and the threaded sleeve 9 prevent additional turning of the dosing device.

Once the last possible dose of the product to be administered has been discharged, i.e. once the carpule 3 is completely empty, the delivery apparatus blocks an additional discharge rotation of the dosing sleeve 11. In this case, the threaded end 8a of the threaded rod 8 comes in contact with the ribs of the internal thread 7g of the threaded nut 7 and prevents an additional axial motion of the threaded rod 8 relative to the threaded nut 7. Since the threaded rod 8 is secured against rotating relative to the housing, the threaded nut 7 and the threaded rod 8 are also prevented from jointly rotating. Consequently, the dosing sleeve 11 is prevented from being additionally screwed in as long as the coupling 10 and the dosing sleeve 11 are secured against rotating relative to one another. If the dose adjusted by the user exceeds the quantity of product remaining in the carpule 3, the non-administered residual quantity can be easily read on the dosing sleeve 11 through the window 9b in the blocked state. This residual quantity can then be administered in another injection process with a replacement injection unit.

FIGS. 5-8 show a second embodiment according to the invention. This second embodiment is, in principle, structured similar to the first embodiment and functions identically for the user. Distinctions can be seen in the reverse lock and in the coupling mechanism between the dosing device and the delivery apparatus. In addition, the second embodiment features an alternative design of the dosing knob.

These changes are elucidated below with reference to FIGS. 5-8. Identical reference symbols in the figures referring to several embodiments mean that the corresponding elements are essentially realized identically in the different embodiments.

Figure 5:
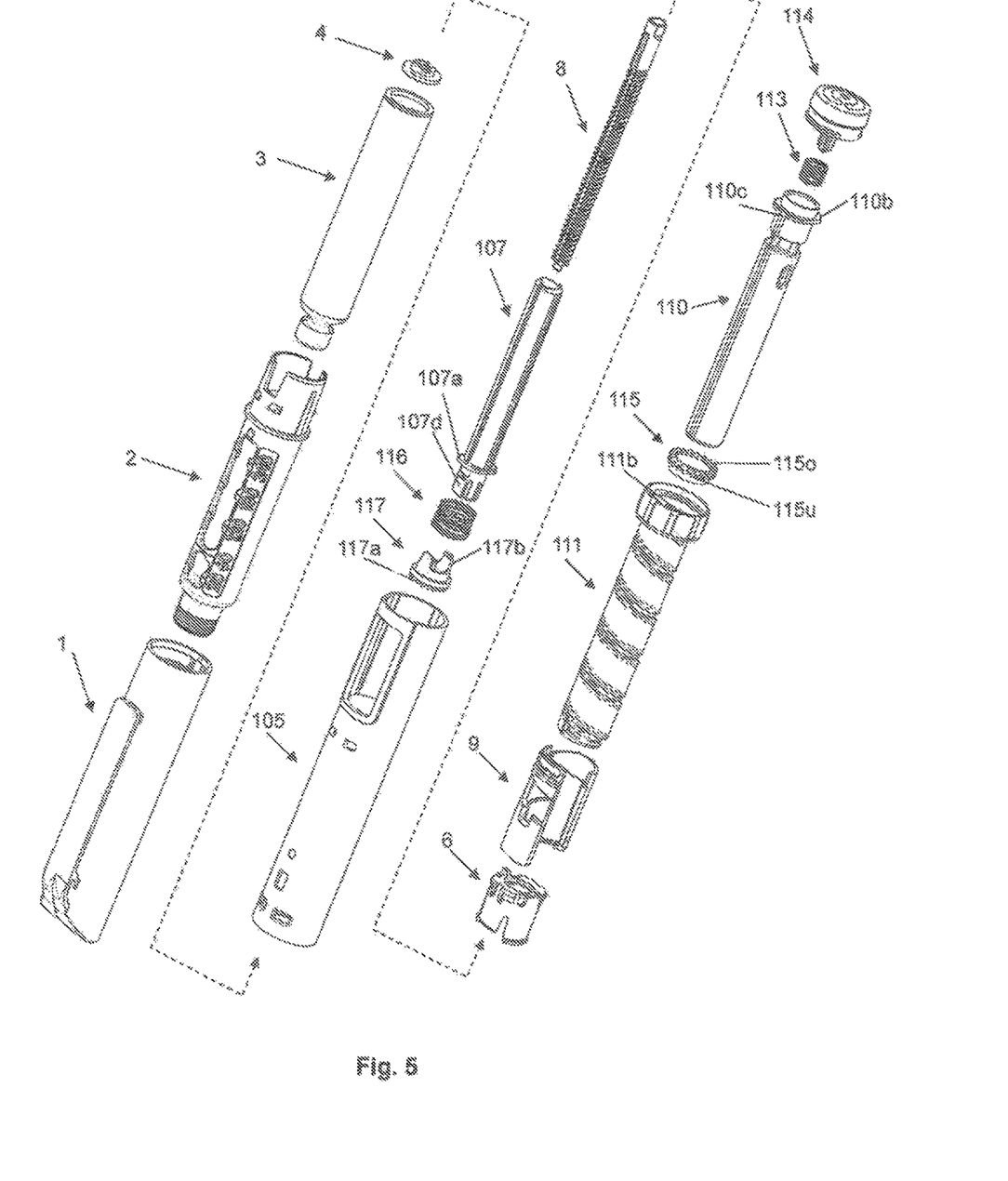
FIG. 5 shows an exploded view of the individual components of a second embodiment of an injection unit according to the invention.
Figures 6, 7, 8:
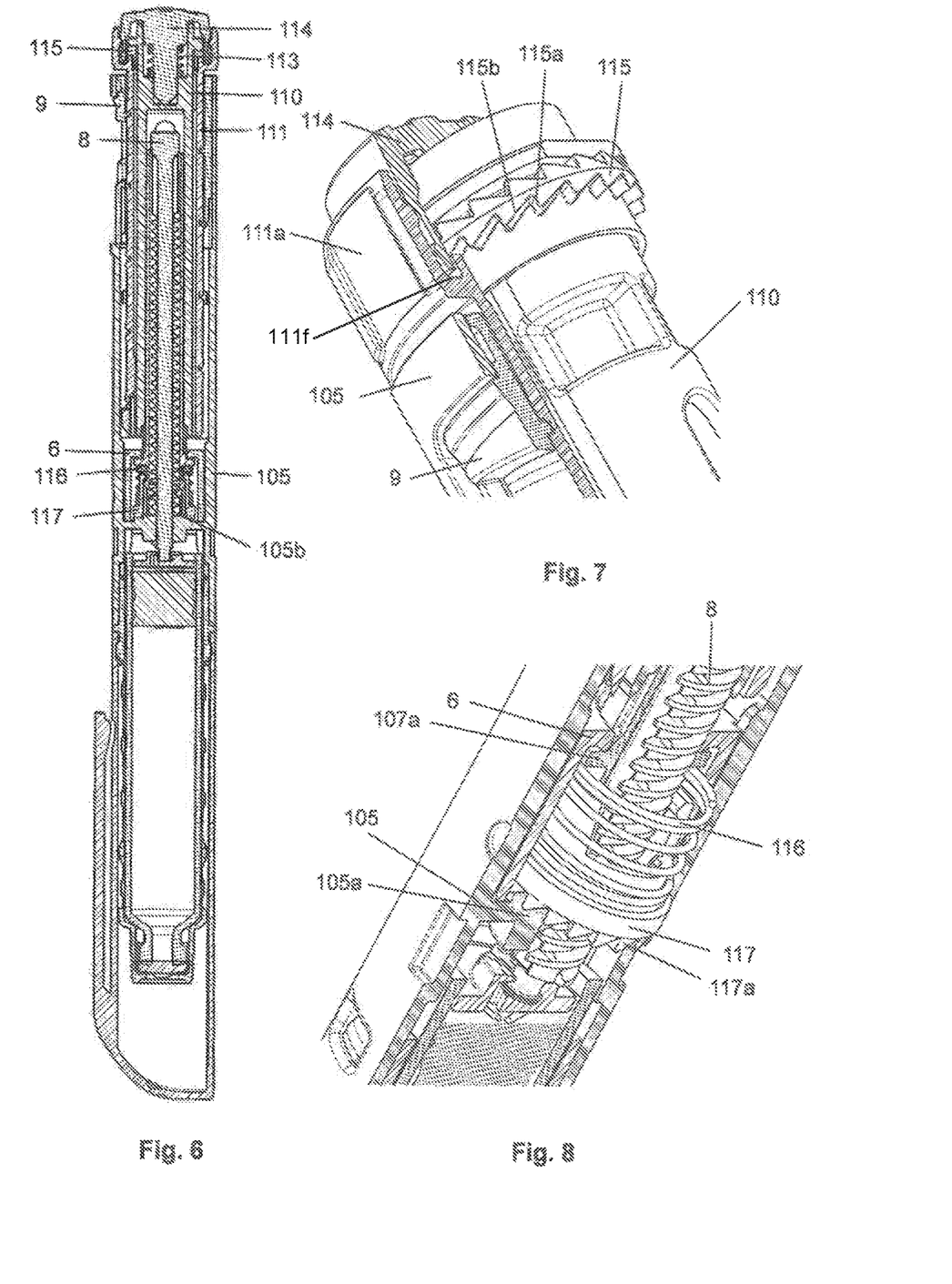
FIG. 6 shows a longitudinal section through the second embodiment in the initial state.
FIG. 7 shows a detail of the coupling arrangement of the second embodiment.
FIG. 8 shows a detail of the reverse lock of the second embodiment.
Figure 9:
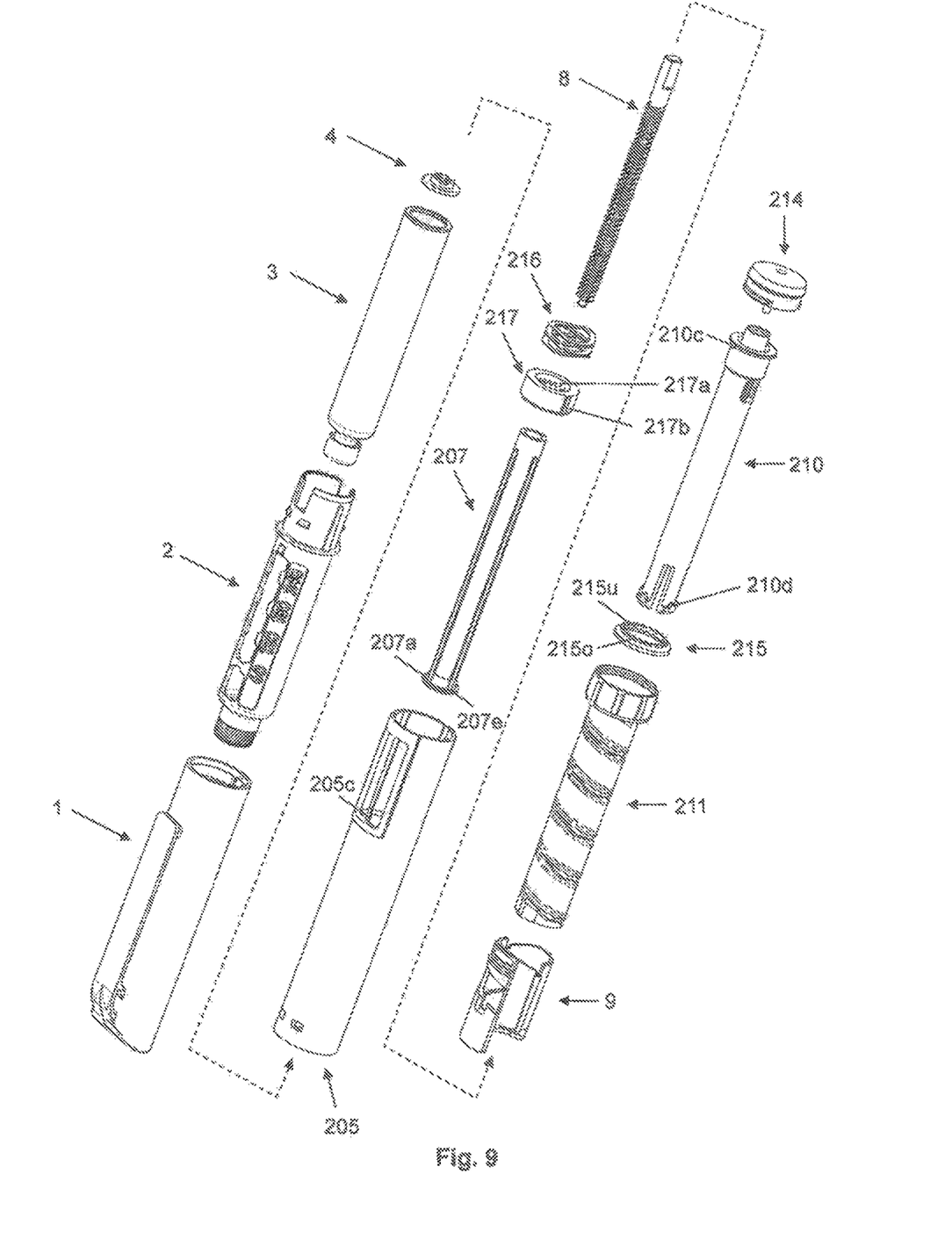
FIG. 9 shows an exploded view of the individual components of a third embodiment of an injection unit according to the invention.
Figure 10:
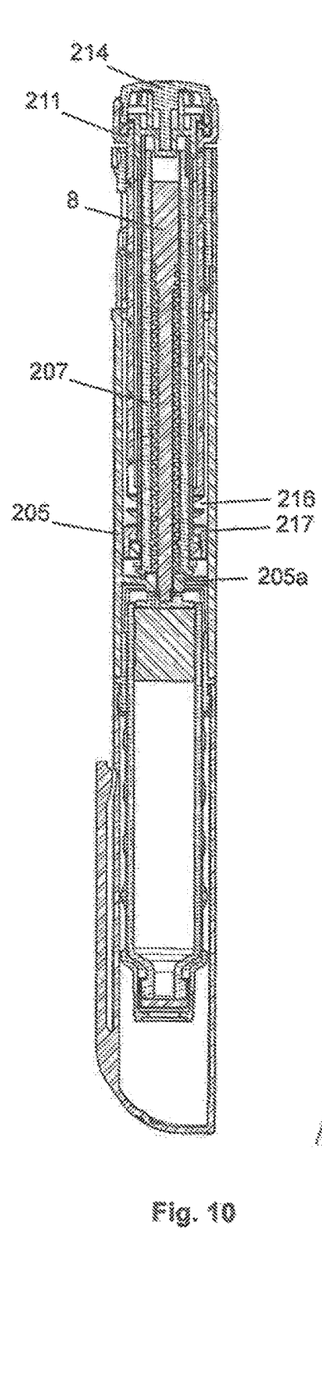
FIG. 10 shows a longitudinal section through the third embodiment in the initial state.
Figure 11:
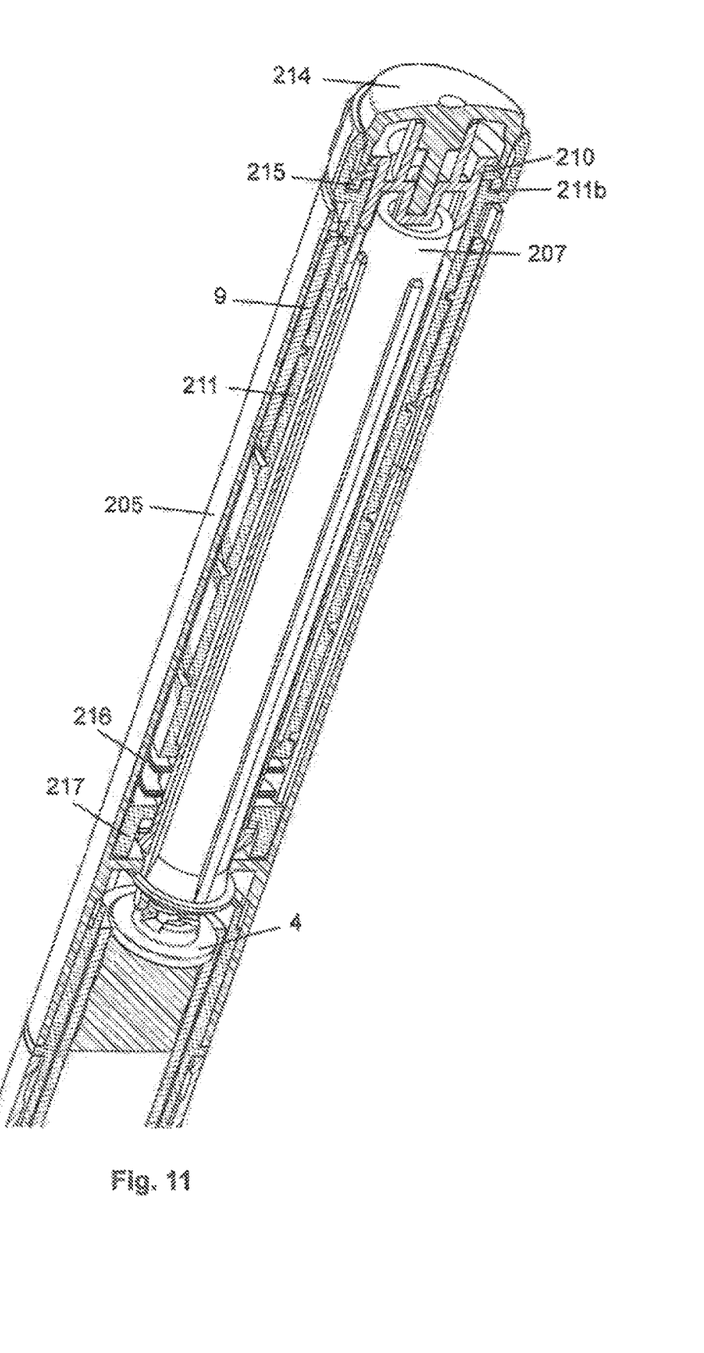
FIG. 11 shows a detail of the coupling arrangement of the third embodiment.

In comparison with the first embodiment, the coupling mechanism between the delivery apparatus and the dosing device in the second embodiment comprises an additional element, namely a click disk 115. The second embodiment comprises a dosing sleeve 111 that is in threaded engagement with the threaded sleeve 9. The coupling mechanism furthermore comprises the coupling 110 that is arranged in the injection unit analogously to the first embodiment. The discharge button 114 and the dosing click-spring 113 function in the same way as in the first embodiment, although they have a different geometric design. In contrast to the first embodiment, the flange 110b and the counterface 111f do not directly engage into one another, but rather are separated from one another by the click disk 115.

As already explained above in the description of the first embodiment, the coupling mechanism fulfills two functions. The first function involves coupling the delivery apparatus and the dosing device and the second function involves respectively generating an acoustic clicking sound or a resistance change that can be perceived in a tactile fashion during the dosing motion and the dose correcting motion. In the first embodiment, the flange 10b and the counterface 11f are realized in the form of a bidirectional coupling, wherein the geometric designs of the toothings 10c and 11b must allow rotation in both directions, but this may be disadvantageous for generating an easily audible clicking sound or a resistance change that can be perceived in a tactile fashion. The second embodiment does not feature a bidirectional coupling in the sense of the first embodiment. The rotational motions in the coupling mechanism between the coupling 110 and the dosing sleeve 111 (e.g. by rotation of rotary knob 111a) take place in a locally separated fashion. The click disk 115 is coaxially arranged between the coupling flange 110b of the coupling 110 and the counterface 111f of the dosing sleeve 111 (analogous to a washer). The two-sided click disk 115 comprises a first and a second coupling face and features a proximal toothing 115o that is engaged with the toothing 110c on the coupling flange 110b and a distal toothing 115u that is engaged with the toothing 111b on the counterface of the dosing sleeve 111. The individual teeth of the toothings 110c, 111b, 115o and 115u preferably have an asymmetric geometric design. FIG. 7 shows a preferred embodiment of the toothing on the click disk 115. In this embodiment, for example, the distal toothing 115u features teeth with a tooth flank 115a that is approximately aligned in the axial direction. The teeth 115u have a second tooth flank 115b that is inclined relative to the axial direction, wherein the angle of inclination of the tooth flank 115b preferably deviates from the axis of the injection unit by more than 0°, but by less than 90°. The teeth of the toothing 115o are preferably realized in an analogous fashion. In an advantageous embodiment, the teeth 115o are aligned in such a way that they are shaped in the form of a mirror image of the toothing 115u referred to a sectional plane that extends perpendicular to the longitudinal axis of the injection unit. The respective toothings 110c and 111b of the coupling 110 and the dosing sleeve 111 that are assigned to the toothings 115o and 115u are realized complementary to the respective toothings 115o and 115u. The described advantageous design of the coupling mechanism between the dosing device and the delivery apparatus results in a separation of the sliding faces that move relative to one another within the coupling mechanism during the dose adjustment on the one hand and the dose correction on the other hand. Due to the asymmetric shape of the teeth 115o, 115u, 110c, 111b, no relative motion can take place between the coupling 110 and the click disk 115 while the dose is increased because the axially directed tooth flanks prevent such a motion. Conversely, the dosing sleeve 111 can be moved relative to the click disk 115 while the dose is increased due to the orientation of the tooth flanks. During a dose correction, this situation is exactly reversed, i.e. a relative motion between the coupling 110 and the click disk 115 is possible and the motion between the dosing sleeve 111 and the click disk 115 is blocked. The dosing spring 113 generates a force that presses the facing toothings of the coupling mechanism into one another. During a relative motion of engaged toothings, the individual teeth are displaced along the tooth flank that is not directed axially and act upon the dosing click-spring 113 with an increasing restoring force. This increased restoring force can be perceived by the user and may serve as tactile feedback. After the tips of the teeth slide over one another, the teeth spring back into their axial starting position along the axially aligned tooth flanks under the influence of the restoring force of the spring. Once the teeth reach the axial starting position, an acoustic signal that is also referred to as a click is generated due to the impact of the of the teeth on one another. Since one of the tooth flanks is aligned axially, a maximum of stored energy of the spring is used for generating the clicking sound during the motion of the teeth into their axial starting position and only a minimum is used for the additional displacement of the teeth relative to one another. In comparison with the first embodiment, the second embodiment of the coupling mechanism between the dosing device and the delivery apparatus illustrated in these figures has the advantage of making it possible to generate acoustic feedback signals that can be perceived in an improved fashion during the dosing operation and the dose correction. Other variations are conceivable, particularly also in connection with the described tactile feedback. For example, the toothings 115u and 115o may feature teeth that have a different height and the same width, wherein the teeth on the dosing sleeve 111 and on the coupling 110 are realized complementary to the assigned teeth on the click disk 115. This refers, in particular, to the axial height of the teeth. Consequently, the dosing click and the dose correction click may be acoustically distinguishable. In another fascinating embodiment, the teeth 115u and 115o may have a different width, particularly a different width referred to the rotational angle. For example, a tooth 115o may be twice as wide as a tooth 115u such that each dose correction click reduces the dose by twice the amount of the dose increase realized with each dosing click.

Analogous to the first embodiment, the threaded nut 107 of the second embodiment is axially fixed relative to the housing 105, but rotatable. A reverse lock furthermore ensures that the threaded nut can only be rotated or turned relative to the housing 105 in one direction. However, the reverse lock in the second embodiment is structured differently than in the first embodiment. On its distal end, the threaded nut 107 is surrounded by an annular toothed disk 117. The toothed disk 117 can be longitudinally displaced relative to the threaded nut 107, but is secured against rotating relative to the threaded nut and arranged coaxial thereto. For this purpose, the toothed disk 117 features guide cams 117b that protrude axially toward the proximal end and are guided in guide surfaces 107d of the threaded nut. The toothed disk 117 furthermore comprises a toothing 117a that protrudes in the distal direction and can engage into a counter-toothing 105b of the piston rod guide 105a provided for this purpose. A turn-back spring 116 supported on the flange 107a presses the toothed disk 117 in the distal direction such that the toothing 117a engages into the counter-toothing 105b with a defined axial force. According to FIG. 8, the toothing 117a is advantageously realized asymmetrically such that a relative rotation between the toothed disk 117 and the housing 105 is possible in one direction and blocked in the other direction. Since the toothed disk 117 is non-rotatably arranged on the threaded nut 107, the threaded nut 107 can also rotate in only one direction. In comparison with the reverse lock of the first embodiment, the reverse lock of the second embodiment has the advantage that its manufacture is less complex. In addition, the reverse lock of the second embodiment is not prone to relaxation phenomena. Another advantage can be seen in that the incorporation of a separate spring makes it possible to vary the rotational resistance of the threaded nut 107 during a rotation in the permitted direction without adaptations of the design by simply selecting an appropriate spring—which is not possible in the first embodiment—such that the acoustic and tactile discharge feedback, as well as the reluctance, can be controlled.

In comparison with the first embodiment, the geometric design of the discharge button 114 is also modified in the second embodiment. However, this geometric modification has no notable effect on the function.

The changes made in the second embodiment in comparison with the first embodiment result in no fundamental differences in the operation for the user.

A third embodiment of the injection unit is illustrated in FIGS. 9-13. The third embodiment is based on the second embodiment. One advantage of the third embodiment in comparison with the second embodiment can be seen in the reduction in the number of required components. One difference between the second and the third embodiment is the modified arrangement of the reverse lock that is no longer positioned on the threaded nut 207 in the third embodiment, but rather on the coupling 210 such that the turn-back spring 216 also functions as a dosing click-spring. The specific details of the third embodiment are elucidated below.

The reverse lock of the third embodiment comprises an annular toothed disk 217 that is supported in the housing 205 in a displaceable but non-rotatable fashion. In this case, the support is realized by means of guide ribs 217b on the toothed disk 217 and guide grooves 205c on the inner side of the housing. The toothed disk 217 comprises an asymmetric toothing 217a that is axially oriented in the distal direction. In the third embodiment, the coupling 210 features on its distal end an asymmetric counter-toothing 210d that is axially oriented in the proximal direction and can be engaged with the toothing 217a. As in the second embodiment, the asymmetric shape of the teeth 217a and 210d serves for permitting relative motions in only one direction. In this case, the turn-back spring 216 ensures that a force acts upon the toothed disk 217 in the distal direction, wherein this force ensures that the toothed disk 217 can be engaged with the toothing 210d on the coupling 210 after the assembly of the injection unit. In the third embodiment, the turn-back spring 216 not only acts upon the toothed disk 217 in the distal direction, but also upon the dosing sleeve 211 in the proximal direction. In the advantageous embodiment shown, the turn-back spring 216 is arranged coaxially outside the coupling 210 and clamped between the distal end of the dosing sleeve 211 and the toothed disk 217. When a dose is adjusted, the toothed disk 217 and the turn-back spring 216 participate in the axial motion of the coupling 210 and the dosing sleeve 211. This arrangement results in the second function of the turn-back spring 216. Since this spring directly presses the dosing sleeve 211 in the proximal direction and indirectly presses the coupling 210 in the distal direction (by means of the toothed disk 217), an effect on the coupling mechanism between the dosing device and the delivery apparatus is also realized. As in the second embodiment, the coupling 210 and the dosing sleeve 211 are coupled to one another by means of a click disk 215. The click disk 215 basically is structured identical to the click disk 115 and also functions in the same way as the click disk 115. Due to the force exerted upon the coupling 210 and the dosing sleeve 211 by the turn-back spring 216, the toothing 210c is engaged with the toothing 215o and the toothing 211b is engaged with the toothing 215u. The second function of the turn-back spring 216 therefore replaces the function of the dosing click-spring 113 in the second embodiment such that a dosing click-spring is no longer required proximate the discharge button 214 in the third embodiment of the injection unit.

Figures 12, 13:
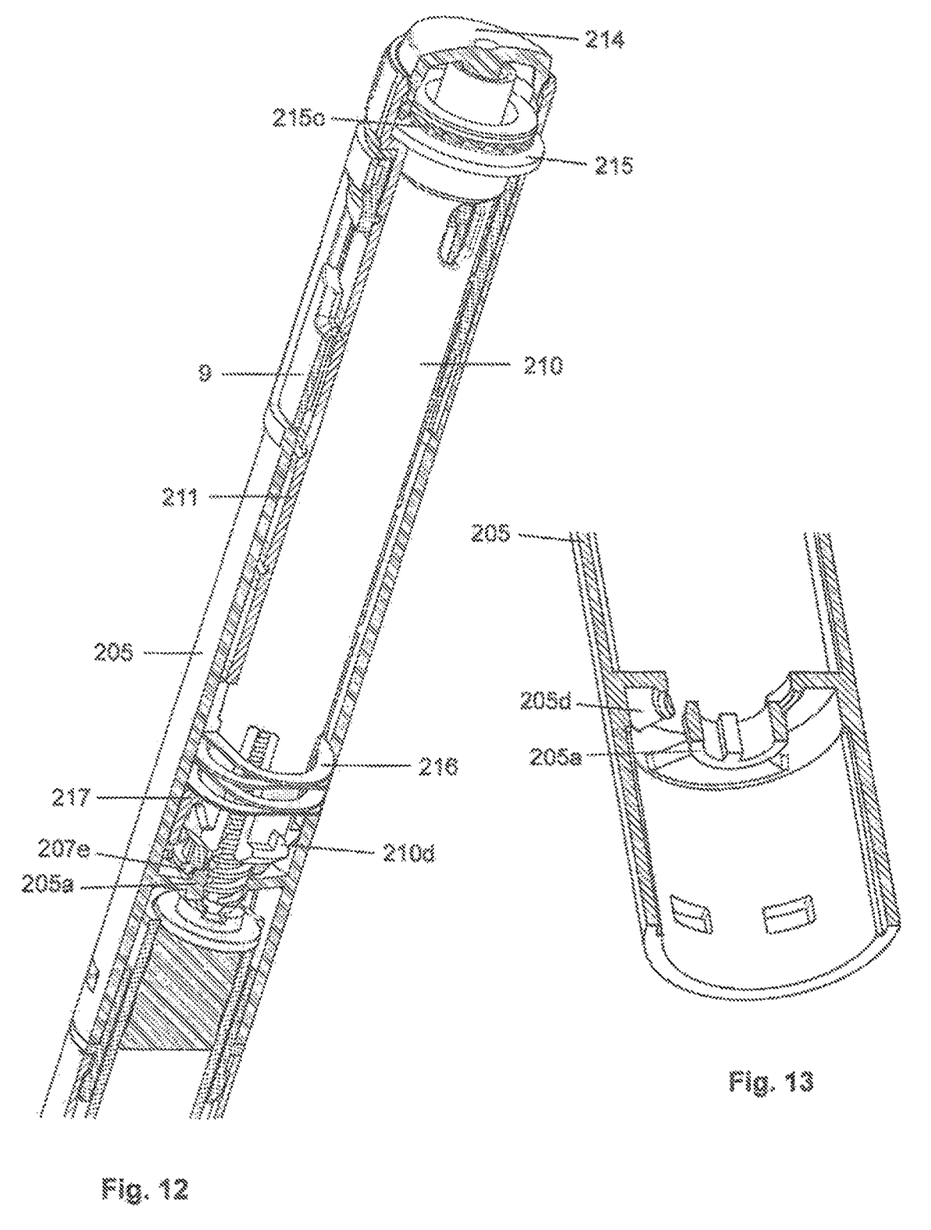
FIG. 12 shows a detail of the reverse lock of the third embodiment.
FIG. 13 shows a detail of the snap fitting for the threaded sleeve of the third embodiment.

According to another simplification of the second embodiment, the housing insert 106 of the second embodiment can be replaced in the third embodiment with a snap fitting 205d that is realized integrally with the housing 205 proximate the piston rod guide 205a as shown in FIG. 13. During the assembly of an injection unit according to the third embodiment, the flange 207a of the threaded nut 207 is during the insertion snapped into the snap fitting 205d of the housing 205. In order to simplify this process, the flange 207a features bevels 207e that initiate the temporary geometric yielding of the snap fitting 205d.

The invention claimed is:

1. An injection unit for administering or delivering a fluid product, the injection unit comprising:
   a housing for a product receptacle;
   a piston rod with an outer thread axially movable and non-rotatably arranged in the housing;
   a delivery apparatus comprising a threaded nut with an inner thread engaged with the outer thread of the piston rod and configured to move the piston rod to deliver the product;
   a dosing device comprising a rotatable dosing sleeve being rotatable in a first direction in a dosing operation to an adjusted dose and in an opposite direction during a dose correction for correcting an inadvertently adjusted excessive dose to a corrected dose; and
   a discharge button arranged on the dosing sleeve,
      wherein a coupling device operatively couples the dosing device to the delivery apparatus to administer or deliver the fluid product,
      wherein the delivery apparatus further comprises an annular toothed disk surrounding the threaded nut in a co-axial arrangement, which toothed disk can be displaced longitudinally relative to the threaded nut but is secured against rotating relative to the threaded nut,
      wherein the toothed disk comprises a toothing protruding in a distal direction and engageable with a counter toothing fixedly arranged in the housing,
      wherein the delivery apparatus further comprising a spring element forcing the toothing of the toothed disk into engagement with the counter toothing, and
      wherein the teeth of the toothing of the toothed disk are shaped asymmetrically such that rotation of the toothed disk and the threaded nut in a first direction, namely during delivery of the product, is possible through sliding of the teeth of the toothing of the toothed disk over the teeth of the counter toothing and rotation of the toothed disk and the threaded nut in a second direction is prevented by the shape of the teeth of the toothing of the toothed disk.

2. The injection device of claim 1, wherein the coupling device comprises at least two coupling faces that are respectively provided with a toothing comprising teeth, and wherein the at least two coupling faces are slidably engaged during the dosing operation or during the dose correction and generate an acoustic and/or tactile signal in accordance with the adjusted dose or the corrected dose of the product to be administered.

3. The injection unit of claim 2, wherein the at least two coupling faces are coupled by a spring.

4. The injection unit of claim 2, wherein each toothing of the at least two coupling faces of the coupling device comprises individual teeth in annular arrangements.

5. The injection unit of claim 2, wherein a relative motion between the at least two coupling faces can be prevented by actuating the discharge button.

6. The injection unit of claim 5, wherein the coupling device comprises a coupling element arranged on the threaded nut in a non-rotatable but axially displaceable fashion, wherein one of the at least two coupling faces is rigidly arranged on the coupling element, and wherein another of the at least two coupling faces is rigidly arranged on the dosing sleeve such that the coupling face of the coupling element and the coupling face of the dosing sleeve can be directly or indirectly engaged with one another.

7. The injection unit of claim 6, wherein the coupling face of the coupling element and the coupling face of the dosing sleeve are indirectly engaged with one another by a click disk, the click disk comprising a first and a second coupling face arranged between the coupling faces of the coupling element and the dosing sleeve, wherein the first coupling face of the click disk comprises a toothing that is complementary to the toothing on the coupling element and the second coupling face of the click disk comprises a toothing that is complementary to the toothing on the dosing sleeve.

8. The injection unit of claim 7, wherein teeth of the toothings of the click disk comprise an asymmetric shape such that a relative motion between the dosing sleeve and the click disk is enabled in one direction and a relative motion between the coupling element and the click disk is enabled in an opposite direction when the discharge button is not actuated.

9. The injection unit of claim 8, wherein the teeth of the toothings on the first and the second coupling faces of the click disk have a different height.

10. The injection unit of claim 8, wherein the teeth of the toothings on the first and the second coupling faces of the click disk have a different width.

* * * * *